United States Patent
Chiang et al.

(10) Patent No.: US 12,232,256 B2
(45) Date of Patent: Feb. 18, 2025

(54) FLEXIBLE HYBRID ELECTRONIC SUBSTRATE AND ELECTRONIC TEXTILE INCLUDING THE SAME

(71) Applicant: Industrial Technology Research Institute, Hsinchu (TW)

(72) Inventors: I-Hung Chiang, Changhua County (TW); Hung-Hsien Ko, Hsinchu County (TW); Min-Hsiung Liang, Hsinchu County (TW); Te-Hsun Lin, Hsinchu (TW); Chen-Tsai Yang, Taoyuan (TW); Hao-Wei Yu, New Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 472 days.

(21) Appl. No.: 17/585,574

(22) Filed: Jan. 27, 2022

(65) Prior Publication Data

US 2023/0147556 A1  May 11, 2023

(30) Foreign Application Priority Data

Nov. 8, 2021 (TW) .................. 110141472

(51) Int. Cl.
*H05K 1/02* (2006.01)
*A61B 5/00* (2006.01)
(Continued)

(52) U.S. Cl.
CPC ........... *H05K 1/038* (2013.01); *A61B 5/6804* (2013.01); *H05K 1/0277* (2013.01)

(58) Field of Classification Search
CPC ........ H05K 1/02; H05K 1/0277; H05K 1/038; H05K 1/189; H05K 3/32; H05K 3/326;
(Continued)

(56) References Cited

U.S. PATENT DOCUMENTS 7,049,559 B2   5/2006  Ishii et al.
8,552,299 B2  10/2013  Rogers et al.
(Continued)

FOREIGN PATENT DOCUMENTS

AU   2003241438   11/2003
CN      111319320    6/2020
(Continued)

OTHER PUBLICATIONS

"Office Action of Taiwan Counterpart Application", issued on Jun. 20, 2022, p. 1-p. 9.
(Continued)

*Primary Examiner* — Xiaoliang Chen
(74) *Attorney, Agent, or Firm* — JCIPRNET

(57) ABSTRACT

A flexible hybrid electronic substrate and electronic textile including the same are provided. The flexible hybrid electronic substrate includes a first region and a second region. There is a joint between the first region and the second region. Each of the first region and the second region includes at least one selected from the group consisting of the following structure features: multilayer structure feature, anisotropic structure feature and pre-strained structure feature.

12 Claims, 5 Drawing Sheets

(51) Int. Cl.
  *H05K 1/03* (2006.01)
  *H05K 3/32* (2006.01)

(58) Field of Classification Search
  CPC ..... A61B 5/0017; A61B 5/746; A61B 5/4839; A61B 5/6802; A61B 5/6804; A61B 5/6805; A61B 5/14532; A61B 5/14552
  USPC .................................. 361/749, 813; 442/205
  See application file for complete search history.

(56) References Cited

U.S. PATENT DOCUMENTS

| | | | |
|---|---|---|---|
| 10,757,804 B1 | 8/2020 | Peng et al. | |
| 2003/0211797 A1* | 11/2003 | Hill | H05K 1/038 442/205 |
| 2006/0038182 A1 | 2/2006 | Rogers et al. | |
| 2010/0302745 A1* | 12/2010 | Hsu | H05K 3/326 361/813 |
| 2017/0173262 A1* | 6/2017 | Veltz | G16H 20/17 |
| 2019/0267756 A1* | 8/2019 | Prot | H01R 12/78 |
| 2020/0404780 A1 | 12/2020 | Liu et al. | |
| 2021/0077304 A1 | 3/2021 | Xu et al. | |
| 2021/0193854 A1 | 6/2021 | Stutterheim et al. | |
| 2022/0053637 A1* | 2/2022 | Aristides | A61B 5/14552 |
| 2022/0287637 A1* | 9/2022 | Chenegros | A61B 5/6804 |

FOREIGN PATENT DOCUMENTS

| | | |
|---|---|---|
| CN | 112367903 | 2/2021 |
| TW | 201709780 | 3/2017 |
| TW | 201825013 | 7/2018 |
| TW | I736363 | 8/2021 |
| WO | 2021077092 | 4/2021 |

OTHER PUBLICATIONS

I-Hung Chiang et al., Abstract of "P-106: An Electromechanical Integration Design Method with Strain Analysis Correlation for Flexible Hybrid Electronics", SID Symposium Digest of Technical Papers, Jun. 28, 2021, p. 1.
"Office Action of China Counterpart Application", issued on Oct. 31, 2024, pp. 1-7.

* cited by examiner

FLEXIBLE HYBRID ELECTRONIC SUBSTRATE AND ELECTRONIC TEXTILE INCLUDING THE SAME

CROSS-REFERENCE TO RELATED APPLICATION

This application claims the priority benefit of Taiwan application serial no. 110141472, filed on Nov. 8, 2021. The entirety of the above-mentioned patent application is hereby incorporated by reference herein and made a part of this specification.

TECHNICAL FIELD

The disclosure relates to an electronic substrate and an electronic textile including the same, and more particularly to a flexible hybrid electronic substrate and an electronic textile including the same.

BACKGROUND

Flexible hybrid electronic (FHE) integrates silicon-based semiconductors and flexible electronics, and has the following advantages: (1) the cost of FHE is lower than that of silicon-based semiconductors; (2) the performance of FHE is better than printed electronics; (3) FHE has better flexibility than silicon-based semiconductors and flexible electronic products. Therefore, FHE is suitable for being integrated into systems with different requirements; (4) FHE is compatible with continuous roll-to-roll manufacturing due to its flexible characteristics.

Due to the requirements for integration of silicon-based semiconductors and flexible electronics, the deformation or distortion of the FHE structure must be taken into account during the movement to ensure reliable product performance when strain occurs. For example, a circuit designed in a high strain region of a flexible hybrid electronic product is likely to cause the circuit between the flexible substrate and the rigid substrate to be easily broken due to high stress.

SUMMARY

According to an embodiment of the disclosure, a flexible hybrid electronic substrate is provided, which includes: a first region; and a second region. There is a joint between the first region and the second region. Each of the first region and the second region includes at least one selected from the group consisting of the following structure features: multilayer structure feature, anisotropic structure feature and pre-strained structure feature.

According to another embodiment of the disclosure, an electronic textile is provided, which includes: a textile; and a flexible electronic device disposed on the textile. The flexible electronic device includes: a substrate; a contact structure provided on the substrate; a device structure provided on the substrate and electrically connected to the contact structure; and a circuit structure provided on the substrate and electrically connect the contact structure and the device structure. The substrate includes a first region and a second region. There is a joint between the first region and the second region. Each of the first region and the second region includes at least one selected from the group consisting of the following structure features: multilayer structure feature, anisotropic structure feature, and pre-strained structure feature.

DETAILED DESCRIPTION OF DISCLOSED EMBODIMENTS

Figure 1:
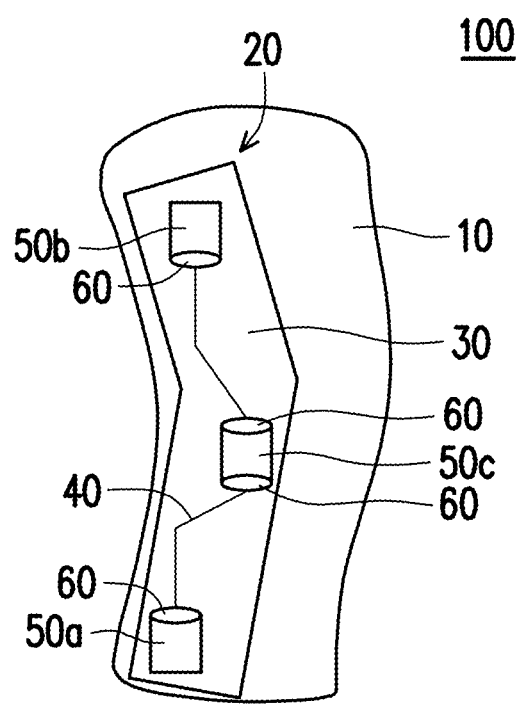
FIG. 1 is a perspective view of an electronic textile according to an embodiment of the disclosure.

FIG. 1 is a perspective view of an electronic textile according to an embodiment of the disclosure.

Please refer to FIG. 1, the electronic textile 100 includes a textile 10 and a flexible electronic device 20 arranged on the textile 10. In this embodiment, "textile" can be interpreted as a flexible material or product made entirely or partly of fibers. The fibers can be provided as single fibers, or can be bundled together into a multi-fiber configuration (such as yarn). In this embodiment, the textile 10 can be used as a cover for the head, torso or limbs.

In an embodiment, the textile 10 may be a textile having a woven structure, a knitted structure, a non-woven structure, or a sandwiched structure. In an embodiment, the material of the textile 10 is, for example, polyurethane (PU), polyethylene (PE), polypropylene (PP) or thermoplastic polyurethane (TPU), but the disclosure is not limited thereto. In an embodiment, the stiffness of the textile 10 is, for example, between 1e3 grams per square second ($g/s^2$) and 1e7 grams per square second ($g/s^2$). In an embodiment, the bending stiffness of the textile 10 is, for example, between 1e2 grams*square millimeter/square second*radian ($g*mm^2/s^2*rad$) and 2e6 grams*square millimeter/square second *radian ($g*mm^2/s^2*rad$).

In an embodiment, the flexible electronic device 20 is a flexible electronic device with a passive function and/or an active function. The flexible electronic device 20 includes a substrate 30 and a circuit structure 40, a device structure 50 and a contact structure 60 on the substrate 30. The substrate 30 is provided to carry the circuit structure 40, the device structure 50 and the contact structure 60 of the flexible electronic device 20. The substrate 30 is, for example, a flexible substrate. The substrate 30 may be a single layer or multiple layers. The substrate 30 may be composed of a single material or multiple materials. The thickness of the substrate 30 is, for example, 0.1 mm to 2 mm.

The substrate 30 includes a single-layer or multi-layer structure of organic or inorganic materials (or referred to as polymers). Organic materials include, for example, one of polyimide (PI), polymethylmethacrylate (PMMA), polycarbonate (PC), polyether sulfide (PES), polyamide (PA), polyethylene terephthalate ester (PET), polyether ether ketone (PEEK), polyethylene naphthalate (PEN), polyethyleneimine (PEI), polyurethane (PU), polydimethylsiloxane (PDMS), acrylic, ether-based polymers, and polyolefin, or a combination of two or more of the above. Inorganic materials include, for example, one of cu foil, glass fiber, and carbon fiber, or a combination of two or more of the above, but the disclosure is not limited thereto. In other words, the substrate 30 may be a single organic material, a mixture of two organic materials, or a mixture of multiple organic materials.

In other embodiments, the substrate 30 is a composite material. The substrate 30 includes organic materials and inorganic materials. The inorganic material can be distributed in the organic material in the form of dots, strips, nets, three-dimensional nets, or a combination thereof. The organic material is as described above. The addition of inorganic materials can improve the impact resistance of the impact-resistant and shock-absorbing structure. The inorganic material may be silica, aluminum oxide, titanic oxide or a combination thereof, but is not limited thereto.

The material of the substrate 30 and the material of the textile 10 may be the same or different. In an embodiment, the material of the substrate 30 is the same as the material of the textile 10. In other words, the textile 10 itself can be used as the substrate 30. In the above case, the substrate 30 and the textile 10 may be integrally formed. In an embodiment, the stiffness of the substrate 30 is, for example, between 1e3 grams per square second ($g/s^2$) and 1e7 grams per square second ($g/s^2$). In an embodiment, the bending stiffness of the substrate 30 is, for example, between 1e2 grams*square millimeter/square second *radian ($g*mm^2/s^2*rad$) and 2e6 grams*square millimeter/square second *radian ($g*mm^2/s^2*rad$).

One or more contact structures 60 are provided on the substrate 30. The contact structure 60 is a structure for connecting material discontinuities in the flexible electronic device 20. In an embodiment, the contact structure 60 is located at the position where the device structure 50 is disposed, and the contact structure 60 is electrically connected to the device structure 50 and the circuit structure 40. In an embodiment, the material of the contact structure 60 is a material with a viscous function before drying. In an embodiment, the contact structure 60 may be solder paste or conductive paste.

In an embodiment, the contact structure 60 is, for example, a redistribution structure. The redistribution structure includes one or more insulating layers and one or more redistribution layers located therein, and part of the redistribution layer forms the circuit contact. The material of the insulating layer includes, for example, polymer, nitride, oxide, or a combination thereof. The polymer is, for example, polybenzoxazole (PBO), polyimide, benzocyclobutene (BCB), or a combination thereof. Nitride includes, for example, silicon nitride and the like. Oxide includes, for example, silicon oxide, phosphosilicate glass (PSG), borosilicate glass (BSG), borophosphosilicate glass (BPSG), or a combination thereof. The material of the redistribution layer includes a conductor, such as a metal or a metal alloy, such as Al, Cu, Sn, Ni, Au, Ag, or other suitable conductive materials. In an embodiment, the contact structure 60 may be formed on the substrate 30 by attaching, pressing, sputtering, printing, electroplating, electroless plating, chemical vapor deposition (CVD), or the like.

One or more device structures 50 may be disposed on the substrate 30. More specifically, the device structure 50 may be a die. The die can be composed of a single or multiple active and/or passive device. The dies are, for example, application-specific integrated circuit (ASIC) chips, analog chips, sensor chips, wireless and radio frequency chips, voltage regulator chips, or memory chips. The device structure 50 may also be a stacked die, a package structure, a package-on-package (PoP), a package-in-package (PiP), and a system-in-package (SiP). In an embodiment, the device structure 50 includes at least one integrated circuit and has a pin terminal.

In an embodiment, the device structure 50 may be adhered to the contact structure 60 through anisotropic conductive adhesive (ACA), anisotropic conductive film (ACF), anisotropic conductive paste (ACP), photosensitive photoresist, tape, solder paste, or a combination thereof. In an embodiment, the device structure 50 may be electrically connected to the circuit contacts of the contact structure 60.

In an embodiment, the device structure 50 may include device structures 50a, 50b, and 50c (as shown in FIG. 1), but it is not limited thereto. Different device structures have different functions. In an embodiment, the device structures 50a and 50b are various sensing devices that can be designed to adapt to various carriers. They are provided to detect events or changes in the environment and send this information to the device structure 50c (such as SiP processor).

In an embodiment, the device structure 50 is a sensor chip (or referred to as a FHE sensor chip). The sensor chip can be a gravity sensor chip, a temperature sensor chip, an electrocardiogram (ECG/EKG) sensor, a photoplethysmography (PPG) sensor, an electromyography (EMG) sensor, a blood pressure meter or other physiological data measurement sensor, or a combination of the above apparatuses, but not limited thereto. In an embodiment, the sensor chip can sense various physiological signals including at least heartbeat, respiration, blood pressure, body temperature, body fat percentage and the like.

A circuit structure 40 is provided on the substrate 30. The circuit structure 40 may be adapted for flexible functional carriers. The circuit structure 40 is provided to electrically connect the contact structure 60 and the device structure 50.

In an embodiment, the circuit structure 40 may be similar to the contact structure 60 as a redistribution structure. In other words, the circuit structure 40 may include an insulating layer and a plurality of circuits (not shown). In an embodiment, multiple circuits are formed in the insulating layer. The material of the insulating layer of the circuit structure 40 may be similar to the material of the insulating layer of the contact structure 60. The multiple circuits include a conductive material, which may be similar to the material of the redistribution layer of the contact structure 60. The contact structure 60 and the circuit structure 40 may be formed on the substrate 30 simultaneously. The circuit structure can electrically connect the contact structure 60 and the device structure 50 located at different positions.

In an embodiment, the circuit structure 40 is a long strip structure having a connection function (connecting the contact structure 60 and the device structure 50) and a bending function. In an embodiment, the circuit structure 40 is, for example, a wire. One end of the circuit structure 40 as the wire is electrically connected to the contact structure 60, and the other end is electrically connected to another contact structure 60. In an embodiment, the insulating layer of the circuit structure 40 and the insulating layer of the contact structure 60 may be formed simultaneously. The multiple circuits of the circuit structure 40 are formed on the insulating layer of the circuit structure 40 after the contact structure is formed. The multiple circuits or wires of the circuit structure 40 can be formed on the substrate 30 by printing, coating, or pressing. In an embodiment, the length of the circuit structure 40 is 1 mm to 2000 mm.

In an embodiment where the application field is a wearable device, when the wearable device is put on and taken off, the strain at the part where the wearable device is put on and taken off (such as the waist where pants are put on) is generally greater than 60%, which is much greater than the strain acceptable for the circuit (the strain acceptable for the circuit needs to be less than 15%). As a result, the reliability of the device will be reduced. In addition, the wiring of wearable devices with active functions (such as heating coils) must go through frequently moving parts (such as joints or knees), and the strain of frequently moving parts is generally greater than 20%, which is also greater than the strain acceptable for the circuit. As a result, the reliability of device will decrease and the feasibility of wiring distribution at this part will also decrease. Moreover, the strain caused by muscle expansion during exercise will also reduce the reliability of the device. Furthermore, the radius of curvature of the device or circuit layout position will also reduce the reliability of the device.

Therefore, in this embodiment, the substrate 30 may have a segmented design to improve the functionality of each part and take into account comfort. Specifically, the substrate 30 may include multiple regions, and each region may have special structure features depending on different functionality and comfort requirements. In an embodiment, the segmentation of the substrate 30 is, for example, lamination, stitching, fastening, zipper, or integral weaving, but the disclosure is not limited thereto. The segmented design of the substrate 30 is described in detail below.

Figure 2:
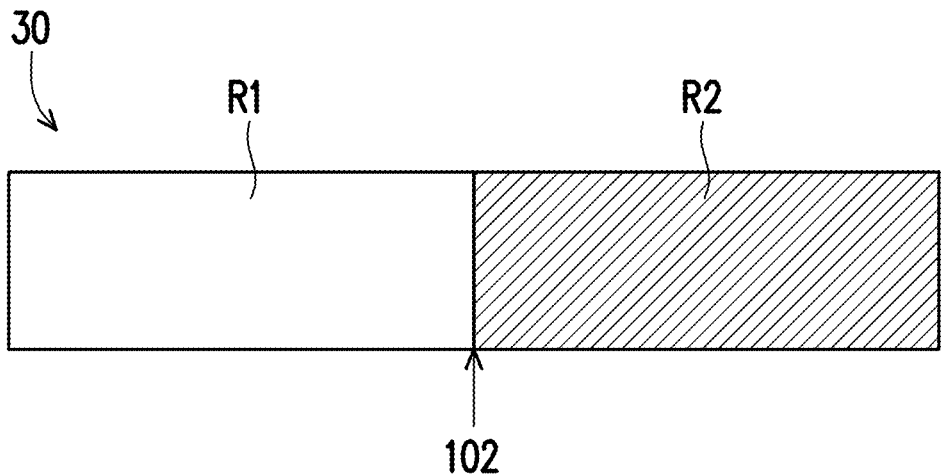
FIG. 2 is a schematic view illustrating the segmented design of the substrate 30 according to an embodiment of the disclosure.

FIG. 2 is a schematic view illustrating the segmented design of the substrate 30 according to an embodiment of the disclosure. Referring to FIG. 2, in an embodiment, the substrate 30 includes a first region R1 and a second region R2, and there is a joint 102 between the first region R1 and the second region R2. The joining methods of the first region R1 and the second region R2 include laminating, stitching, fastening, zipper or integral weaving. In this embodiment, each of the first region R1 and the second region R2 includes at least one selected from the group consisting of the following structure features: multilayer structure feature, anisotropic structure feature, and pre-strained structure feature.

In this embodiment, the multilayer structure feature includes multilayer stacking, increased thickness, or patterning. In this embodiment, stacking a substrate (or another textile) on a textile (textile can be used as a part of the substrate) is a feature of "multi-layer stacking". In this embodiment, the feature of "increased thickness" means that the thickness of a specific region of the substrate (or textile) is greater than the thickness of other regions. In this embodiment, the feature of "patterning" means that there are holes in a specific region of the substrate so that the substrate in the specific region can be divided into an upper layer and a lower layer. In addition, the feature of "patterning" can also mean that a specific region of the substrate has silicone dot fillers with different distribution densities. In this embodiment, the strain of the region of the substrate 30 with the multilayer structure feature is less than 15%.

In an embodiment, the region of the substrate 30 with the multilayer structure feature can be applied to a wearing part or a frequently moving part. In an embodiment, the region of the substrate 30 with the multilayer structure feature can be applied to the waist, knee, elbow, or hip, but the disclosure is not limited thereto.

In an embodiment where the application field is a wearable knee pad, when there is only a single layer of cloth in the knee area, when the knee is bent to 100 degrees, the strain on the front and peripheral of the knee is greater than 20%, which will affect the feasibility of wiring. However, if the single-layer cloth at the front of the knee is changed to have a multilayer structure feature (for example, a double-layer cloth area is stitched at the front of the knee), the strain on the forward path can be effectively reduced and the comfort can be maintained (strain can be reduced to 10%, and the stress is less than 0.52 kPa).

In an embodiment, the anisotropic structure feature can be achieved by changing the warp and weft density. In another embodiment, the anisotropic structure feature can be achieved by an anisotropic arrangement caused by weaving or stretching. For example, the directions of warp and weft yarn can be different by knitting textile, or the directions of warp and weft yarn can be different by stretching the substrate. An anisotropic material can limit the amount of strain in a specific direction of movement. In an embodiment, the strain of the region of the substrate 30 with anisotropic structure feature is less than 15%.

In an embodiment, the region of the substrate 30 with anisotropic structure feature may be applied to a wearing part or a frequently moving part. In an embodiment, the region of the substrate 30 with anisotropic structure feature may be applied to the waist, knee, elbow, or hip, but the disclosure is not limited thereto.

In an embodiment where the application field is a wearable knee pad, the single-layer cloth at the front of the knee is changed to have the anisotropic structure feature (for example, the strength at warp of the front knee pad is changed to be 4 times the original), the strain on the forward path can be effectively reduced and the comfort can be maintained (strain can be reduced to 15%, and the stress is less than 0.52 kPa).

In an embodiment, pre-strain can be applied to the textile as the substrate to obtain the pre-strained structure feature. In another embodiment, pre-strain may be applied to the textile as the substrate first, and then the pre-strained textile is attached to the substrate to obtain the pre-strained structure feature. In this embodiment, the region of the substrate with pre-strained structure feature can increase the comfort of movement and reduce the stress and strain in this region. Taking cycling pants as an example of the application field, pre-strained cycling pants can reduce the strain on the front part of the thigh from 20% to about 5% during cycling.

In an embodiment, the region of the substrate 30 with pre-strained structure feature can be applied to a frequently moving part. In an embodiment, the region of the substrate 30 with pre-strained structure feature can be applied to the waist, knee, elbow, or hip, but the disclosure is not limited thereto.

In an embodiment where the application field is a wearable knee pad, the cloth at the knee is changed to have the pre-strained structure feature (for example, the loosened cloth is stitched on the front side of the knee), the stress on the forward path can be effectively reduced and the comfort can be maintained (stress can be reduced from 100% to 70% or less).

In this embodiment, the structure feature of the first region R1 and the structure feature of the second region R2 may be the same or different. In an embodiment, the first region R1 includes a multilayer structure feature, and the second region R2 includes an anisotropic structure feature. In an embodiment, the first region R1 includes a multilayer structure feature, and the second region R2 includes a pre-strained structure feature. In an embodiment, the first region R1 includes anisotropic structure feature, and the second region R2 includes pre-strained structure feature.

In an embodiment, both the first region R1 and the second region R2 include multilayer structure feature, but the multilayer structure feature of the first region R1 is different from the multilayer structure feature of the second region R2. In an embodiment, the first region R1 has a multilayer structure feature of "multi-layer stacking", and the second region R2 has a multilayer structure feature of "patterning". In an embodiment, the first region has a "patterning" multilayer structure feature, and the second region R2 has an "increased thickness" multilayer structure feature. In another embodiment, both the first region R1 and the second region R2 include the multilayer structure feature of "multi-layer stacking", but the materials stacked in the first region R1 and the second region R2 are different.

Figure 3:
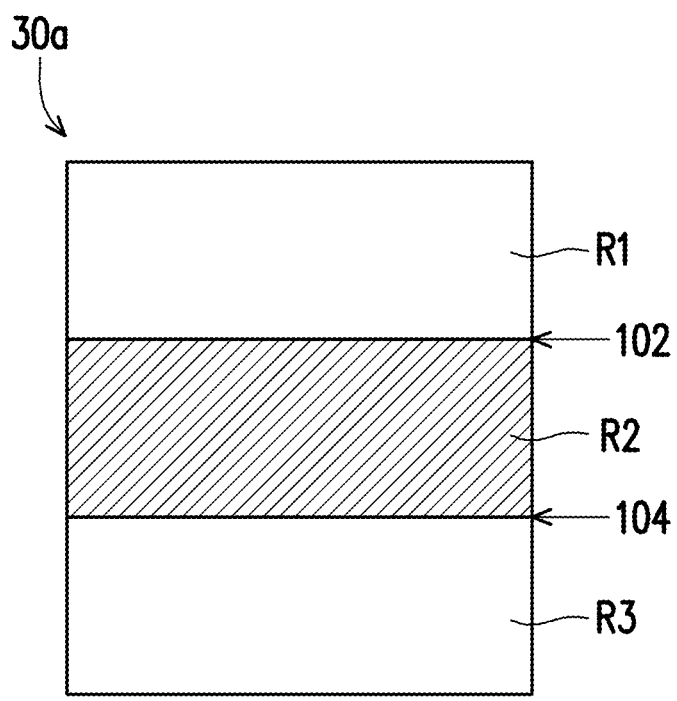
FIG. 3 is a schematic view illustrating the segmented design of the substrate 30a according to an embodiment of the disclosure.

FIG. 3 is a schematic view illustrating the segmented design of the substrate 30a according to an embodiment of the disclosure. Referring to FIG. 3, in an embodiment, the substrate 30a includes a first region R1, a second region R2, and a third region R3, and there is a joint 102 between the first region R1 and the second region R2, and there is a joint 104 between the second region R2 and the third region R3. In this embodiment, each of the first region R1, the second region R2, and the third region R3 includes at least one selected from the group consisting of the following structure features: multilayer structure feature, anisotropic structure feature, and pre-strained structure feature. Each region can have special structure features depending on different functions and comfort requirements. Details about this embodiment that are similar to those of the foregoing embodiment will not be repeated here.

In this embodiment, the structure feature of the first region R1, the structure feature of the second region R2, and the structure feature of the third region R3 may be the same or different. Each region can have special structure features depending on different functions and comfort requirements.

Figure 4:
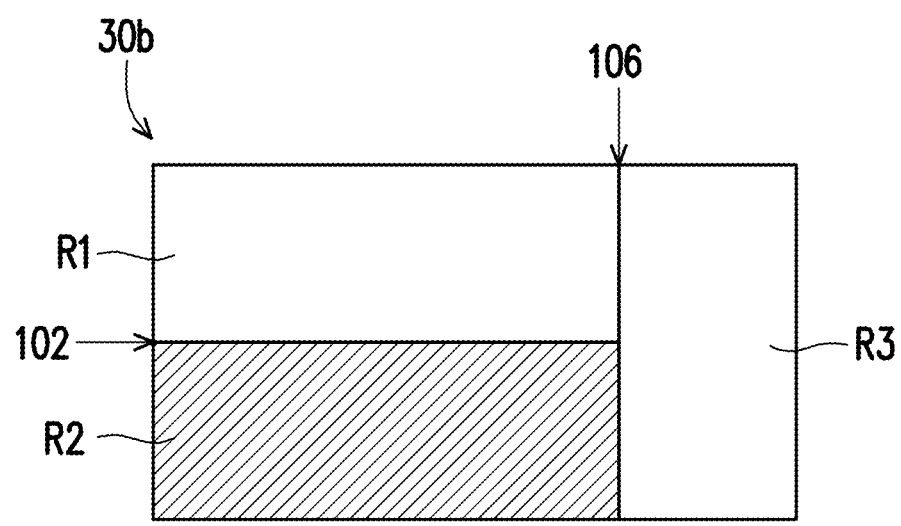
FIG. 4 is a schematic view illustrating the segmented design of the substrate 30b according to an embodiment of the disclosure.

FIG. 4 is a schematic view illustrating the segmented design of the substrate 30b according to an embodiment of the disclosure. Referring to FIG. 4, in an embodiment, the substrate 30b includes a first region R1, a second region R2, and a third region R3, and there is a joint 102 between the first region R1 and the second region R2, and there is a joint 106 between the third region R3 and the first region R1 as well as the second region R2. In this embodiment, each of the first region R1, the second region R2, and the third region R3 includes at least one selected from the group consisting of the following structure features: multilayer structure feature, anisotropic structure feature, and pre-strained structure feature. The structure feature of the first region R1, the structure feature of the second region R2, and the structure feature of the third region R3 may be the same or different. Each region can have special structure features depending on different functions and comfort requirements. Details about this embodiment that are similar to those of the foregoing embodiment will not be repeated here.

The segmented design of the substrate shown in FIG. 2 to FIG. 4 is only for exemplary purpose, and is not intended to limit the disclosure. In other embodiments, there may be other joining methods or the number of regions with structure features may be changed according to requirements (for example, there may be a fourth region, a fifth region, etc.).

Hereinafter, the experimental examples of the disclosure are listed to more concretely establish the disclosure. However, without departing from the spirit of the disclosure, the materials, use methods, etc. shown in the following experimental examples can be appropriately changed. Therefore, the scope of the disclosure should not be limited and interpreted by the experimental examples shown below.

First Embodiment

Figure 5A:
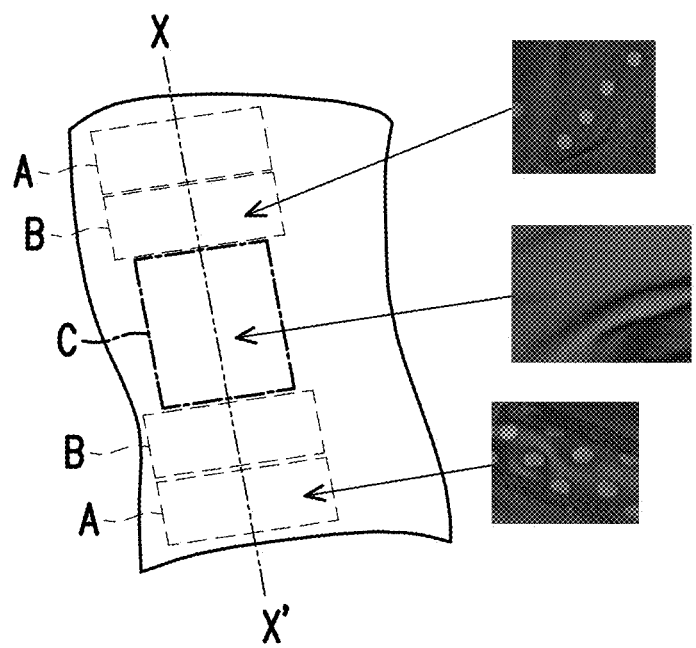
FIG. 5A is a schematic view of a smart knee pad of the first embodiment of the disclosure.
Figure 5B:
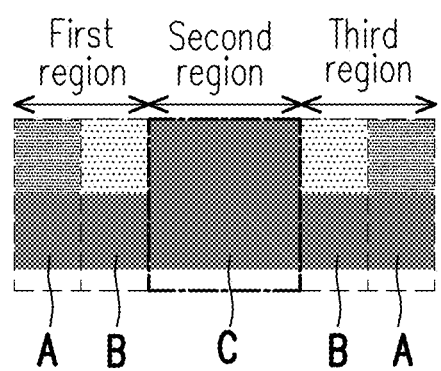
FIG. 5B shows a cross-sectional view of the smart knee pad according to the first embodiment of the disclosure, taken along the line X-X' of FIG. 5A.

FIG. 5A is a schematic view of a smart knee pad of the first embodiment of the disclosure. FIG. 5B shows a cross-sectional view of the smart knee pad according to the first embodiment of the disclosure, taken along the line X-X' of FIG. 5A.

In this embodiment, a single-layer cloth, a double-layer cloth, a silicone dot cloth A, and a silicone dot cloth B are used to fabricate smart knee pads. In this embodiment, the double-layer cloth is formed by stacking another single-layer cloth on a single-layer cloth. The material of the single-layer cloth is 80% polyamide fiber and 20% elastic fiber (polyurethane). The silicone dot cloth is a cloth with silicone dots. The silicone dots are two-dimensional hexagonal fillers. The spacing, diameter, and thickness of the silicone dots are 10 mm, 5 mm, and 0.8 mm, respectively. The difference between the silicone dot cloth A and the silicone dot cloth B is that the silicone dot distribution density of the silicone dot cloth B is 50% of that of the silicone dot cloth A. In this embodiment, different segments are connected by stitching. In this embodiment, the devices are mainly located in segment A and segment B, and the knee position and circuit are mainly located in segment C.

In this embodiment, the concept of segmented design in FIG. 3, for example, is used to fabricate the smart knee pad of the first embodiment. Please refer to FIG. 5A and FIG. 5B. The segment A and segment B on the left side of FIG. 5B constitute the first region R1 described above (for example, the first region R1 in FIG. 3), and the segment C of FIG. 5B constitutes the second region R2 described above (for example, the second region R2 in FIG. 3), and the segment A and segment B on the right side of FIG. 5B constitute the third region R3 described above (for example, the third region R3 in FIG. 3). The interior of segment A of the smart knee pad is a multi-layer structure of single-layer cloth and silicone dot cloth A. The interior of segment B of the smart knee pad is a multi-layer structure of single-layer cloth and silicone dot cloth B. The interior of segment C of the smart knee pad is double-layer cloth. The exteriors of segment A, segment B, and segment C are all composed of single-layer cloth.

First Comparative Example

Figure 6:
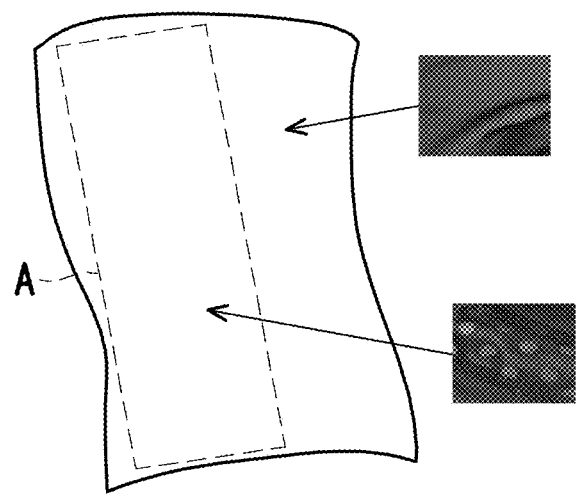
FIG. 6 is a schematic view of the smart knee pad of the first comparative example in the disclosure.

FIG. 6 is a schematic view of the smart knee pad of the first comparative example in the disclosure.

In this embodiment, a single-layer cloth and a silicone dot cloth A are used to fabricate smart knee pads. Please refer to FIG. 6. The interior of segment A of the smart knee pad is a multi-layer structure of single-layer cloth and silicone dot cloth A. In this embodiment, the devices, circuits, and knee positions are mainly located in segment A.

Second Comparative Example

Figure 7:
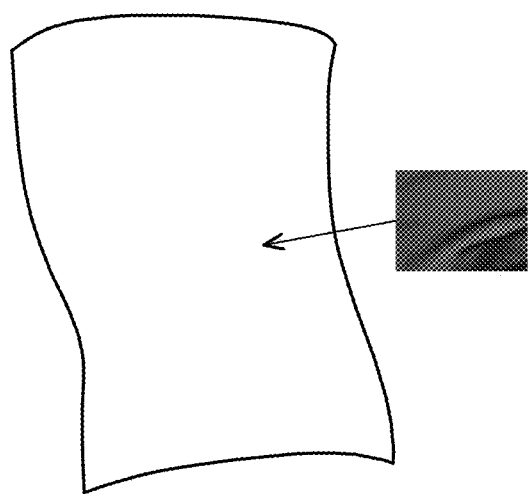
FIG. 7 is a schematic view of the smart knee pad of the second comparative example in the disclosure.

FIG. 7 is a schematic view of the smart knee pad of the second comparative example in the disclosure. In this embodiment, only a single-layer cloth is used to fabricate smart knee pads.

The cloth parameters of the single-layer cloth, the silicone dot cloth A and the silicone dot cloth B are shown in Table 1 below.

TABLE 1

| Cloth parameters | Single-layer cloth | Silicone dot cloth A | Silicone dot cloth B |
|---|---|---|---|
| Weight (g) | 2.34 | 2.43 | 2.39 |
| Weft stiffness (g/s$^2$) | 27323 | 113591 | 70457 |
| Warp stiffness (g/s$^2$) | 39703 | 20597 | 30150 |
| Forward-oblique stiffness (g/s$^2$) | 28435 | 36605 | 32520 |
| Bending stiffness Weft (g * mm$^2$/s$^2$ * rad) | 199 | 194 | 197 |
| Bending stiffness Warp (g * mm$^2$/s$^2$ * rad) | 136 | 81 | 109 |
| Bending stiffness Oblique (g * mm$^2$/s$^2$ * rad) | 215 | 442 | 329 |
| Internal resistance (a.u.) | 0.0001 | 0.0001 | 0.0001 |
| Density (g/mm$^3$) | 118.18 | 225 | 171.6 |
| Friction (a.u.) | 0.03 | 0.03 | 0.03 |
| Thickness (mm) | 0.54 | 0.83 | 0.83 |

Next, stress at 100-degree bending and strain at 100-degree bending of the smart knee pads in the first embodiment and the first and second comparative examples were tested. The results are shown in Table 2 below.

TABLE 2

| | First embodiment | First comparative example | Second comparative example |
|---|---|---|---|
| stress at 100-degree bending (kPa) | 0.33 | 0.34 | 0.62 |
| strain at 100-degree bending | 14.5% | 18.2% | 22.1% |

It can be seen from Table 2 that the stress at 100 degrees of bending of the smart knee pad in the second comparative example reaches 0.62 kPa, which is greater than the comfort pressure of the human knee (about 0.52 kPa). Therefore, the smart knee pad in the second comparative example will cause discomfort to people. In addition, the strain at 100 degrees of bending of the smart knee pad in the second comparative example is 22.1%, which is higher than the strain threshold (15%) acceptable for the circuit, which will reduce the reliability of the device and reduce the feasibility of wiring distribution at this part.

In addition, since the smart knee pad in the first comparative example has a region with multilayer structure feature, the smart knee pad in the first comparative example can improve level of comfort. However, the strain at 100 degrees of bending of the smart knee pad in the first comparative example is 18.2%, which is higher than the strain threshold acceptable for the circuit, which will reduce the reliability of the device and reduce the feasibility of wiring distribution at this part.

However, the smart knee pad in the first embodiment of the disclosure has a segmented design, which includes two regions with structure feature. Therefore, the smart knee pad in the first embodiment has a strain (14.5%) less than 15% and a stress (0.33 kPa) less than 0.52 kPa, thereby satisfying the feasibility of wiring distribution while taking into account comfort.

In summary, since the flexible hybrid electronic substrate using the electronic textile of the disclosure includes multiple regions with segmented design, each region can have a special structure feature depending on different functionalities and comfort requirements. Therefore, comfort can be taken into consideration while the functionalities of various parts can be satisfied.

Although the disclosure has been disclosed in the above embodiments, it is not intended to limit the disclosure. Anyone with ordinary knowledge in the technical field can make some changes and modification without departing from the spirit and scope of the disclosure. Therefore, the scope to be protected by this disclosure shall be subject to the scope of the attached claims.

What is claimed is:

1. An electronic textile, comprising:
    a textile; and
    a flexible electronic device disposed on the textile, wherein the flexible electronic device comprises:
        a substrate;
        a contact structure provided on the substrate;
        a device structure provided on the substrate and electrically connected to the contact structure; and
        a circuit structure provided on the substrate and electrically connecting the contact structure and the device structure,
    wherein the substrate comprises a first region and a second region, there is a joint between the first region and the second region,
    wherein each of the first region and the second region comprises at least one selected from a group consisting of the following structure features: a multilayer structure feature, an anisotropic structure feature, and a pre-strained structure feature,
    wherein a stiffness of the substrate is between 1e3 grams per square second (g/s$^2$) and 1e7 grams per square second (g/s$^2$).

2. The electronic textile according to claim 1, wherein the multilayer structure feature comprises multilayer stacking, increased thickness, or patterning.

3. The electronic textile according to claim 1, wherein a bending stiffness of the substrate is between 1e2 grams*square millimeter/square second *radian (g*mm$^2$/s$^2$*rad) and 2e6 grams*square millimeter/square second *radian (g*mm$^2$/s$^2$*rad).

4. The electronic textile according to claim 1, wherein the textile itself serves as the substrate.

5. The electronic textile according to claim 1, wherein a stiffness of the textile is between 1e3 grams per square second (g/s$^2$) and 1e7 grams per square second (g/s$^2$).

6. The electronic textile according to claim 1, wherein a bending stiffness of the textile is between 1e2 grams*square millimeter/square second *radian (g*mm$^2$/s$^2$*rad) and 2e6 grams*square millimeter/square second *radian (g*mm$^2$/s$^2$*rad).

7. The electronic textile according to claim 1, wherein the device structure comprises an integrated circuit.

8. The electronic textile according to claim 1, wherein a length of the circuit structure is 1 mm to 2000 mm.

9. The electronic textile according to claim 1, wherein the structure feature of the first region is the same as the structure feature of the second region.

10. The electronic textile according to claim 2, wherein the first region and the second region both comprise the multilayer structure feature, the multilayer structure feature of the first region is the patterning, and the multilayer structure feature of the second region is the increased thickness.

11. The electronic textile according to claim 10, wherein the device structure is arranged on the first region, and the circuit structure is arranged on the second region.

12. The electronic textile according to claim 1, wherein the structure feature of the first region is different from the structure feature of the second region.

\* \* \* \* \*